(12) United States Patent
Bittar

(10) Patent No.: US 10,912,960 B1
(45) Date of Patent: Feb. 9, 2021

(54) HYBRID MASK AND FILTER WITH AN ACID CHAMBER AND ULTRAVIOLET SOURCE

(71) Applicant: Tom Bittar, Milltown, NJ (US)

(72) Inventor: Tom Bittar, Milltown, NJ (US)

( * ) Notice: Subject to any disclaimer, the term of this patent is extended or adjusted under 35 U.S.C. 154(b) by 0 days.

(21) Appl. No.: 16/901,465

(22) Filed: Jun. 15, 2020

(51) Int. Cl.
*A62B 23/02* (2006.01)
*A62B 18/02* (2006.01)
*A61L 9/20* (2006.01)
*A61L 9/14* (2006.01)

(52) U.S. Cl.
CPC .............. *A62B 23/02* (2013.01); *A61L 9/145* (2013.01); *A61L 9/20* (2013.01); *A62B 18/02* (2013.01); *A61L 2209/12* (2013.01); *A61L 2209/14* (2013.01); *A61L 2209/213* (2013.01)

(58) Field of Classification Search
CPC ... A61L 9/145; A61L 9/05; A61L 9/14; A61L 9/18; A61L 9/20; A61L 9/22; A61L 9/00; A61L 2209/00; A61L 2209/10; A61L 2209/11; A61L 2209/111; A61L 2209/12; A61L 2209/13; A61L 2209/133; A61L 2209/134; A61L 2209/14; A61L 2209/21; A61L 2209/212; A61L 2209/213; A61L 2209/22; A62B 7/10; A62B 23/00; A62B 23/02; A62B 23/025; A62B 23/04; A62B 23/06; A62B 18/00; A62B 18/02; A62B 18/025; A62B 18/10
See application file for complete search history.

(56) References Cited

U.S. PATENT DOCUMENTS

| | | | | |
|---|---|---|---|---|
| 7,081,225 B1* | 7/2006 | Hollander | ............... | A61L 2/10 210/748.11 |
| 7,404,401 B1* | 7/2008 | Brady | ............... | A62B 7/10 128/205.27 |
| 2003/0111075 A1* | 6/2003 | Wen | ............... | A62B 23/02 128/201.22 |
| 2007/0163588 A1* | 7/2007 | Hebrank | ............... | A61M 16/0051 128/204.18 |
| 2010/0282263 A1* | 11/2010 | Asada | ............... | A62B 7/10 128/206.15 |
| 2010/0307332 A1* | 12/2010 | Yuen | ............... | B03C 3/60 95/26 |
| 2010/0316534 A1* | 12/2010 | Niazi | ............... | A61L 9/145 422/122 |
| 2014/0154134 A1* | 6/2014 | Leyva | ............... | A61M 16/0816 422/28 |

(Continued)

*Primary Examiner* — Jan Christopher L Merene
*Assistant Examiner* — Brian T Khong
(74) *Attorney, Agent, or Firm* — Walter J. Tencza, Jr.

(57) ABSTRACT

A housing having an inner chamber; one or more channels within the housing; one or more inlet ports for allowing air into the one or more channels; each inlet port having a filter to filter air allowed into the one or more channels; the one or more channels connected so that the same air can flow through all of the one or more channels; a pool of electrolyzed high acidity water in the inner chamber of the housing; and wherein contaminants in air flowing through the one or more channels are configured to fall into the pool of electrolyzed water. The apparatus may further include an ultraviolet light source; wherein the ultraviolet light source is directed at air flowing in the one or more channels to cause contaminants in the air to be killed. A mask may be configured to attach and detach from the one or more channels.

20 Claims, 6 Drawing Sheets

(56) References Cited

U.S. PATENT DOCUMENTS

| | | | | |
|---|---|---|---|---|
| 2014/0209454 | A1* | 7/2014 | Ishii | A01N 59/00 |
| | | | | 204/229.6 |
| 2015/0190604 | A1* | 7/2015 | Lin | A61M 16/122 |
| | | | | 128/202.26 |
| 2015/0367356 | A1* | 12/2015 | Gruenbacher | B05B 1/24 |
| | | | | 239/135 |
| 2016/0361454 | A1* | 12/2016 | Minamio | A61L 9/145 |
| 2017/0165445 | A1* | 6/2017 | Zereshkian | A62B 18/003 |
| 2017/0189727 | A1* | 7/2017 | Hunter | A62B 18/02 |
| 2017/0216552 | A1* | 8/2017 | Goff | A61M 16/16 |
| 2019/0255367 | A1* | 8/2019 | Zereshkian | B03C 1/30 |

\* cited by examiner

HYBRID MASK AND FILTER WITH AN ACID CHAMBER AND ULTRAVIOLET SOURCE

FIELD OF THE INVENTION

This invention relates to air filters to be worn with masks to protect individuals from viruses.

BACKGROUND OF THE INVENTION

There are various known masks and filters for protecting individuals from viruses and other contaminants.

SUMMARY OF THE INVENTION

In at least one embodiment of the present invention, an apparatus is provided comprising: a housing having an inner chamber; one or more channels within the housing; one or more inlet ports for allowing air into the one or more channels; wherein each inlet port has a filter to filter air allowed into the one or more channels; wherein the one or more channels are connected so that the same air can flow through all of the one or more channels; a pool of electrolyzed water in the inner chamber of the housing; and wherein contaminants in air flowing through the one or more channels are configured to fall into the pool of electrolyzed water preferably having a high acidity to catch the virus and kill the virus.

In at least one embodiment of the present invention, the apparatus may further include an ultraviolet light source within at least one of the one or more channels; wherein the ultraviolet light source is directed at air flowing in the one or more channels to cause contaminants in the air to be killed.

In at least one embodiment of the present invention, a mask is configured to attach and detach from the one or more channels.

At least one of the one or more channels may have an open end which is inserted into the pool of electrolyzed water typically having a high acidity; and wherein the open end of the at least one of the one or more channels has a filter.

A method is also provided, which may include filtering one or more contaminants out of air flowing into an inner chamber of a housing; and causing one or more contaminants to fall into a pool of electrolyzed water typically having a high acidity in the inner chamber of the housing. The method may also include causing one or more contaminants in the inner chamber of the housing to be killed by ultraviolet light and electrolyzed high acidity water.

DETAILED DESCRIPTION OF THE DRAWINGS

Figure 1:
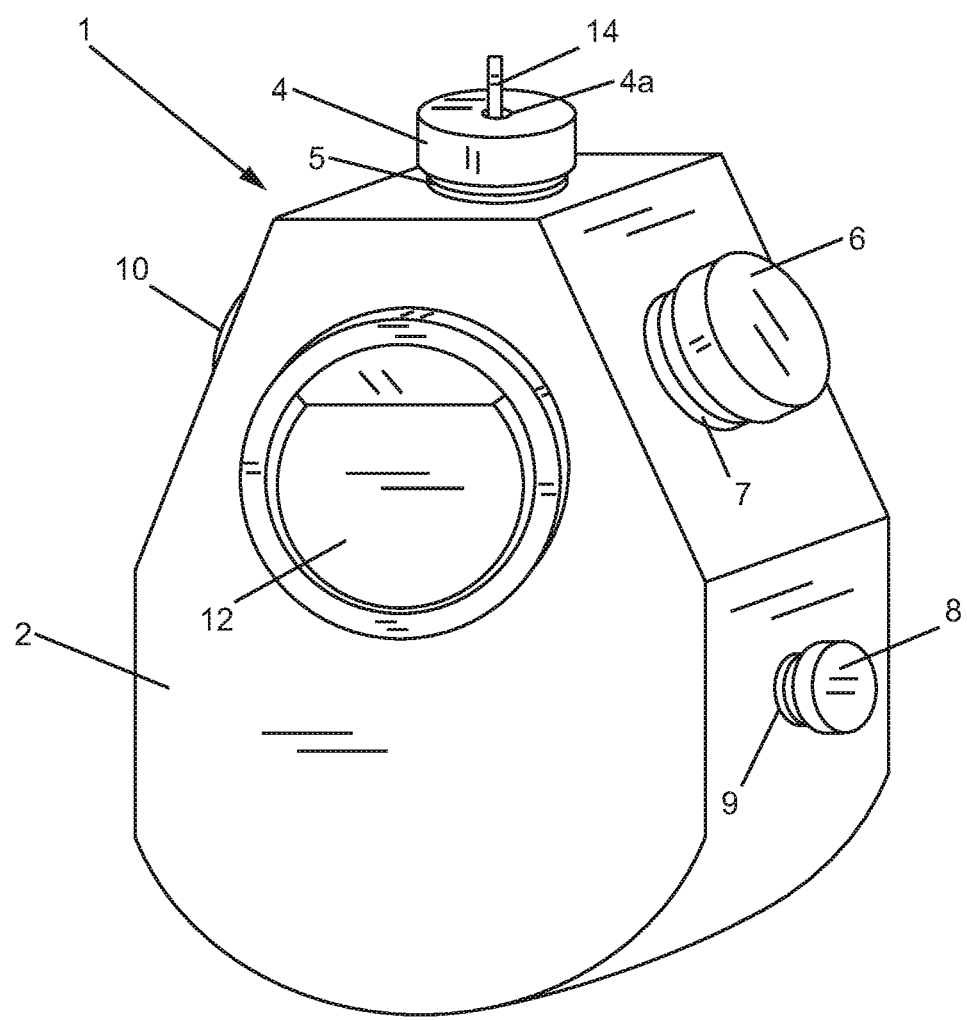
FIG. 1 shows a top, front, and right side perspective view of an apparatus in accordance with an embodiment of the present invention, with the apparatus shown in a first state.
Figure 2:
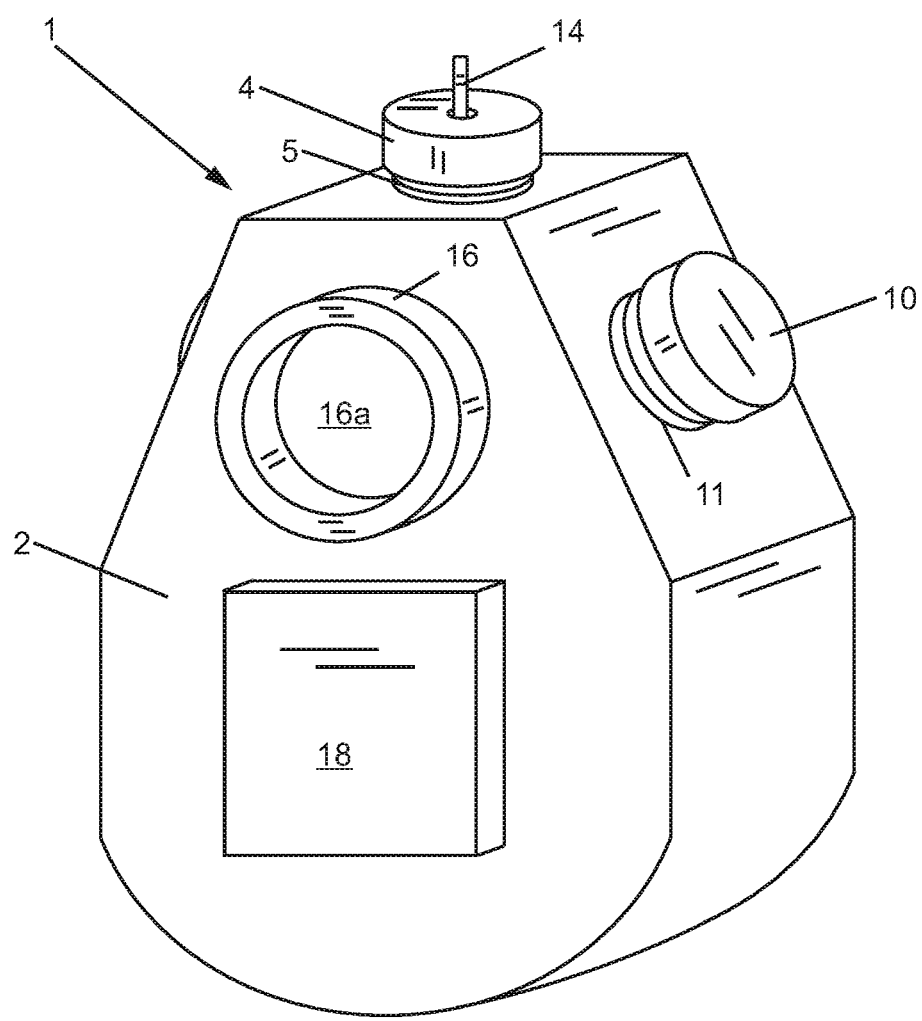
FIG. 2 shows a top, rear, and left side perspective view of the apparatus of FIG. 1 in the first state.
Figure 3:
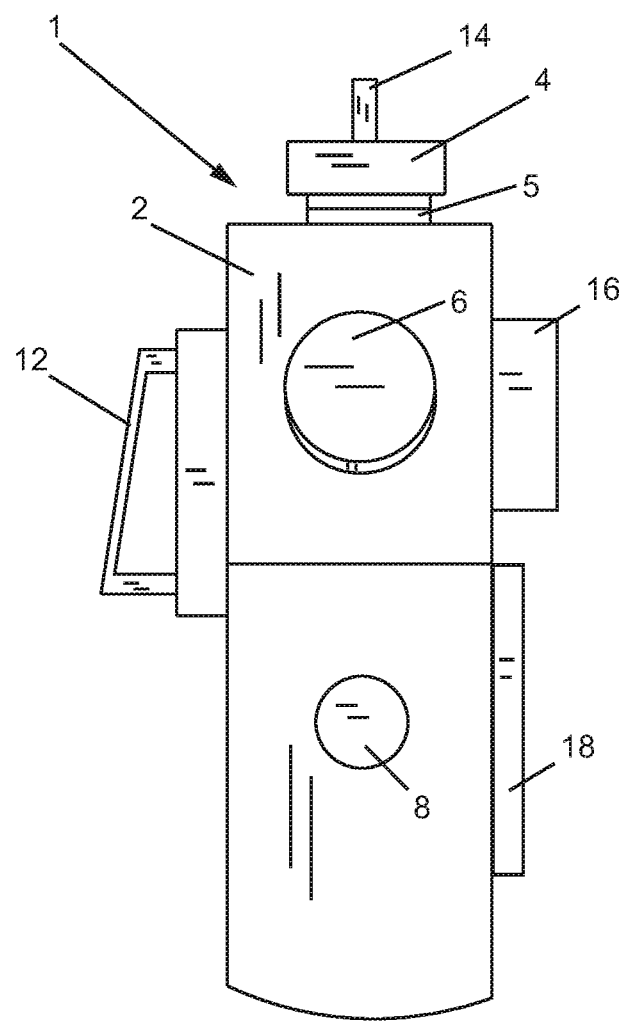
FIG. 3 shows a right side elevational view of the apparatus of FIG. 1 in the first state.
Figure 4:
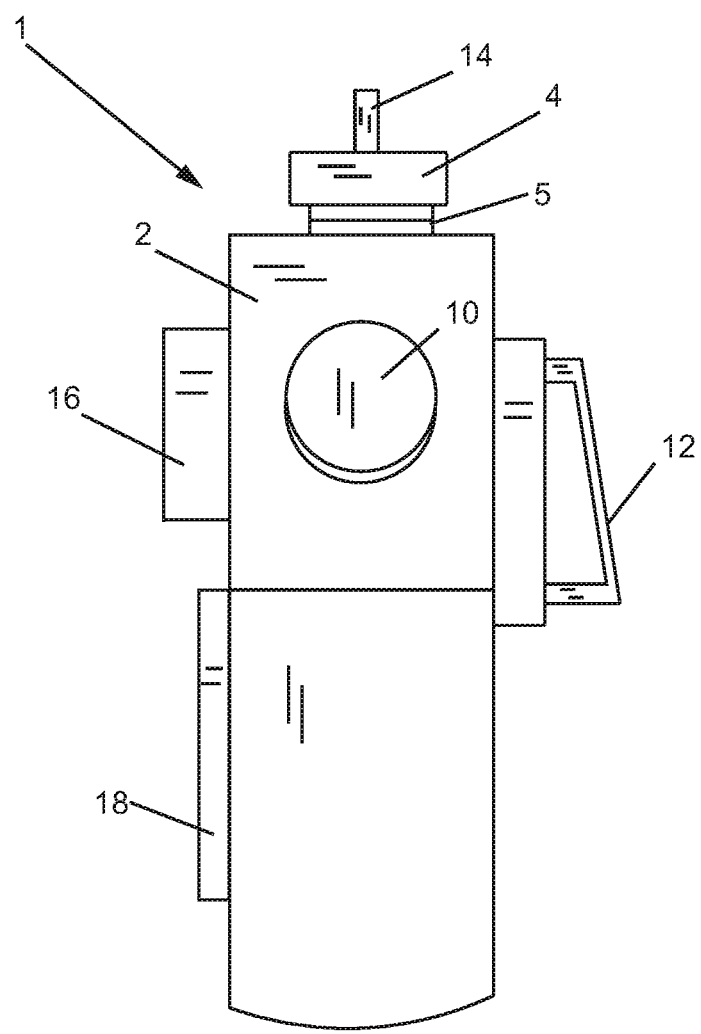
FIG. 4 shows a left side elevational view of the apparatus of FIG. 1 in the first state.

FIG. 1 shows a top, front, and right side perspective view of an apparatus 1 in accordance with an embodiment of the present invention, with the apparatus 1 shown in a first state. FIG. 2 shows a top, rear, and left side perspective view of the apparatus 1 of FIG. 1 in the first state. FIG. 3 shows a right side elevational view of the apparatus 1 of FIG. 1 in the first state. FIG. 4 shows a left side elevational view of the apparatus 1 of FIG. 1 in the first state.

Referring to FIGS. 1-4, the apparatus 1 includes a housing 2, caps 4, 6, 8, and 10. The apparatus 1 further includes extensions or tubes 5, 7, 9, and 11, which are integrated with and/or attached to the housing 2. Each of the extensions or tubes 5, 7, 9, and 11 has outer threads, which are configured to mesh with a corresponding cap, of caps 4, 6, 8, and 10 to removably attach and detach the caps 4, 6, 8, and 10 from the extensions or tubes 5, 7, 9, and 11, respectively.

The cap 8 can be removed to permit electrolyzed water to be added to water 36 or subtracted from water 36 through tube 9.

Figure 6:
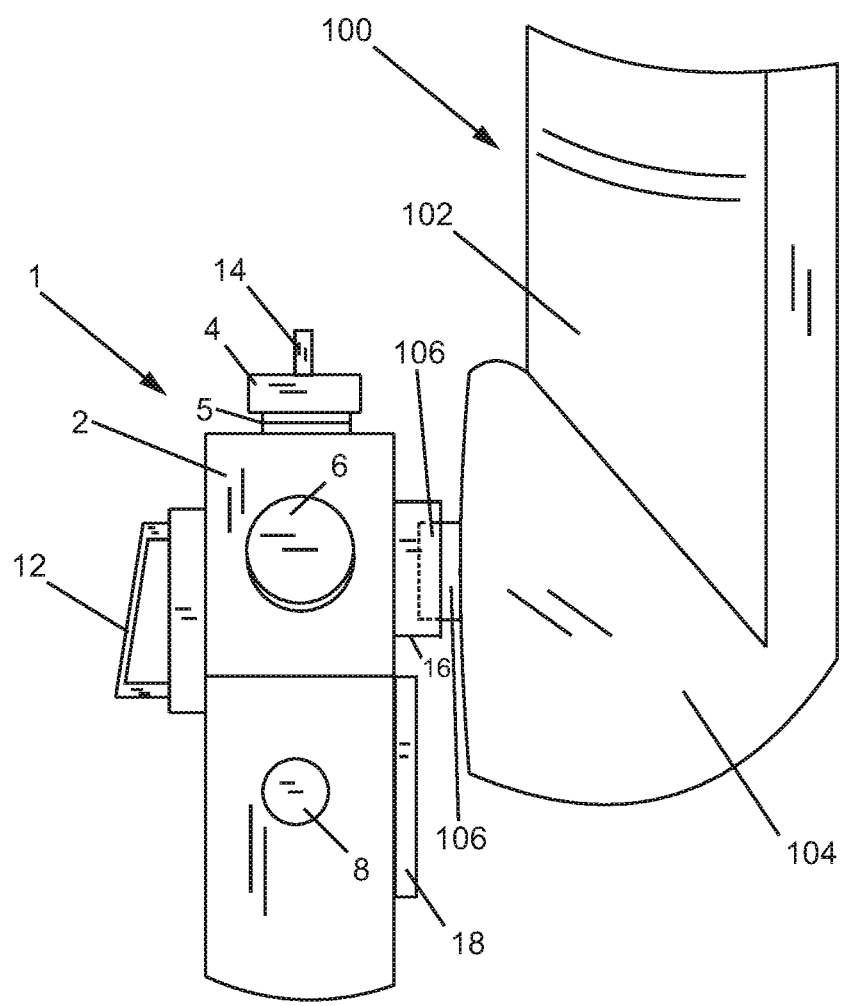
FIG. 6 shows a right side elevational view of the apparatus of FIG. 1 in the first state connected to a mask in accordance with an embodiment of the present invention.

The apparatus 1 further includes a tube or extension 16 configured to be attached to a tube, extension or opening of a mask 100, as shown in FIG. 6. The tube or extension 16 may have a central circular opening 16a for allowing air to pass from an inner chamber of housing 2 of the apparatus 1, through the opening 16a, through an opening of tube 106, into the mask 100, so the air can be breathed by a person wearing make 100.

The apparatus 1 further includes an extension or device 12 which may include a valve for allowing air to escape from an inner chamber of the housing 2 to outside of the housing 2.

Figure 5:
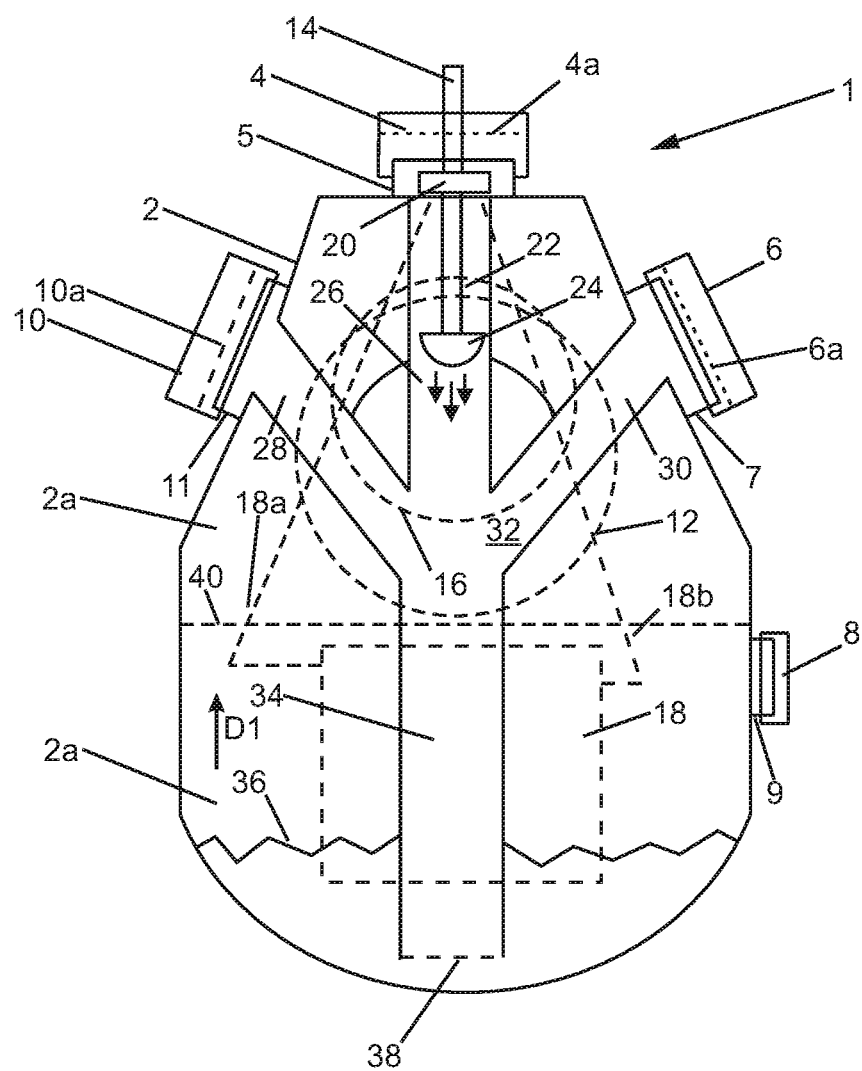
FIG. 5 shows a simplified sectional view of the apparatus of FIG. 1, in the first state, with various internal components shown.

The apparatus 1 further includes a switch 14 which passes through an opening 4a of the cap 4. The switch 14 is configured to be electrically connected to a device or switch 20 shown in FIG. 5. FIG. 5 shows a simplified sectional view of the apparatus 1 of FIG. 1, in the first state, with various internal components shown. The device or switch 20 is electrically connected to two conductors or wires 22 which are connected to a light or light source 24. The switch 20 is connected by conductors 18a and 18b (shown by dashed lines, and may be integrated within housing 2) to battery 18. In at least one embodiment, the light switch 14 is flipped to an "on" position to cause ultraviolet light to be emitted as rays 26 shown in FIG. 5 in a channel, tube or branch 34, and at junction 32, to destroy viruses that may be breathed in through filters 10a and 6a, of caps 10 and 6 respectively, through tubes or branches 28 and 30, respectively, shown in FIG. 5.

As shown in FIG. 5, the apparatus 1 includes tube or branch 28, tube or branch 30, tube or branch 34, and junction 32 where tubes or branches 28, 30, and 34 meet. The tube 34 extends into water 36, which is preferably electrolyzed water preferably having a high acidity held in an inner chamber 2a of the housing 2 of the apparatus 1. Each of the components 28, 30, 32, and 34 may be substantially cylindrical hollow tubes or portions of substantially cylindrical hollow tubes through which air can pass.

In the first state, shown in FIG. 5, the caps 4, 6, 8, and 10 are held and/or screwed tightly on their respective tubes or extensions 5, 7, 9, and 11. In the first state, air can enter the inner chamber 2a through small openings in filters 6a and 10a within caps 6 and 10, respectively, which permit air to enter branches or tubes 30 and 28. In the first state air can exit the inner chamber 2a through the device 12 or valve 12 but cannot enter the inner chamber 2a through the valve or device 12. In the first state air, air enters through filters 6a and 10a, passes through tubes 30 and 28, respectively, where impurities or contaminants are killed by light source 24 and that somewhat purified air and/or impurities falls down into tube 34, and out filter 38 at an end of tube 34, into water 36. Bubbles of air from water 36 move upwards in direction D1, into tube 16, through tube 106 and into mask 100. In addition, air flows out from water 36 through the valve 16.

The tube 16 is not in direct fluid communication with the tubes 28, 30, or 34 or junction 32, rather the air taken in by the tube 16 comes from the water 36, and flows, within the inner chamber 2a, but on the outside of components 28, 30, 32, and 34, and then into tube 16, out opening 16a, into tube 106 and into mask 100. Similarly, the device or valve 12 is not in direct fluid communication with the tubes 28, 30, or 34 or junction 32, rather air flows from the water 36, outside of the components 28, 30, 32, and 34, within the chamber 2a, and out the valve 12.

Air passing through filter 10a goes into tube 28, then into junction 32, where viruses are killed by light source 24. Various impurities that may exist in junction 32 are attracted and/or fall down into water 36 through tube or branch 34.

Air passing through filter 6a goes into tube 30, then into junction 32, where viruses are killed by light source 24. Various impurities that may exist in junction 32 are attracted and/or fall down into water 36 through tube or branch 34.

FIG. 6 shows a right side elevational view of the apparatus 1 of FIG. 1 in the first state connected to the mask 100 in accordance with an embodiment of the present invention. The mask 100 may include a housing 104 and a clear or transparent visor 102. The mask may also include a tube 106 configured to connect within the tube 16 of the apparatus 1.

The apparatus 1 also includes a stainless steel mesh or stainless steel filter 38 (shown in dashed lines in FIG. 5), which may be a fifty micron filter show at the bottom of tube 34 in FIG. 5. The filter 38 is configured in at least one embodiment, to filter out impurities from the electrolyzed high acidity water 36.

The apparatus 1 also includes a filter 40, whose location is shown by dashed lines in FIG. 5. The filter 40 may be a filter fabric which allows air to pass through the filter 40, coming from the water 36, but does not allow water to pass through. The filter 40 may be rectangular in shape and it is critical in at least one embodiment that the filter 40 cover the entire area above the water 36, except for a central circular area, typically where the tube 34, which may be cylindrical tube goes through the filter 40, inside of the inner chamber 2a of the apparatus 1. The filter 40 prevents and/or substantially inhibits water 36 from travelling into tubes 16 106, and into the mask 100. The filter is lower than the valve or device 12 and the tube 16 to avoid water going out the valve 12 or into the tube 16.

When the caps 4, 6, 8, and 10 are secured tightly on the housing 2, and the mask 100 is attached as in FIG. 6, the inner chamber 2a is completely or substantially sealed, so that air can get in only through filters 6a and 10a, purified or substantially purified air can be breathed in by a user using mask 100 through tube 16, and air can be exhausted through valve 12.

The electrolyzed high acidity water 36 kills contaminants, such as viruses. The electrolyzed water 36 has high acidity. In at least one embodiment, the air going into the mask 100 through tube 106 has been filtered of contaminants, such as viruses, substantially and/or completely.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. An apparatus comprising:
a housing having an inner chamber;
one or more channels within the housing;
one or more inlet ports for allowing air into the one or more channels;
wherein each inlet port has a filter to filter the air allowed into the one or more channels;
wherein the one or more channels are connected so that the air can flow through all of the one or more channels;
a pool of electrolyzed water in the inner chamber of the housing; and
wherein contaminants in the air flowing through the one or more channels are configured to fall into the pool of electrolyzed water;
wherein the one or more channels include a first channel and a second channel;
wherein the first channel has a first end and an opposing second end;
wherein a first inlet port of the one or more inlet ports is located at the first end of the first channel;
wherein the first channel and the second channel meet at a junction;
wherein the junction is located nearer the second end of the first channel than the first end of the first channel;
wherein the junction is between an ultraviolet source and a first end of the second channel;
wherein the first end of the second channel lies in the pool of electrolyzed water;
wherein the inner chamber of the housing is separated into a top portion and a bottom portion by a water filter which inhibits the pool of electrolyzed water within the bottom portion of the inner chamber from coming into the top portion of the inner chamber; and
wherein the first channel and the junction lie entirely in the top portion of the inner chamber of the housing.

2. The apparatus of claim 1, further comprising:
a mask configured to attach and detach from the one or more channels.

3. The apparatus of claim 1, wherein:
the first end of the second channel is inserted into the pool of electrolyzed water; and
wherein the first end of the second channel has the water filter.

4. The apparatus of claim 1, wherein
the water filter is configured to cover an entire surface area of the pool of electrolyzed water, from one end of the housing to an opposite end of the housing, except for an area where the first end of the second channel is inserted into the pool of electrolyzed water.

5. The apparatus of claim 4, wherein
the area where the first end of the second channel is inserted into the pool of electrolyzed water is central in the inner chamber.

6. The apparatus of claim 1, wherein
the apparatus is configured so that ambient the air comes in through the first inlet port, passes through the first channel, passes through the junction into the second channel, and is modified in the second channel to form a first modified air;

wherein the apparatus is configured so that the first modified air passes through the second channel, passes out the first end of the second channel and out of the second channel into the pool of electrolyzed water; and wherein the apparatus is configured so that the pool of electrolyzed water modifies the first modified air to form a second modified air, and the second modified air passes through the pool of electrolyzed water and out of the pool of electrolyzed water, passes through the water filter and into a tube, passes through the tube, and out of the inner chamber of the housing.

7. The apparatus of claim 1, wherein there is a gap lying outside of the second channel, between the second channel and the housing, within the inner chamber of the housing; and wherein the air is configured to flow from the pool of electrolyzed water through the gap, into a tube, and out of the housing; and wherein the tube is outside of the first channel, outside of the second channel, and the tube is not directly connected to the first channel or the second channel, such that the air leaving the second channel through the first end of the second channel passes through the pool of electrolyzed water, outside of the second channel, and through the gap, outside of the second channel, to go into the tube, and exit the housing through the tube.

8. The apparatus of claim 1, further comprising an impurities filter separate from the water filter; and wherein the impurities filter is located at the first end of the second channel, and is configured to filter out impurities from the pool of electrolyzed water.

9. An apparatus comprising:

a housing having an inner chamber;

one or more channels within the housing;

one or more inlet ports for allowing air into the one or more channels;

wherein each inlet port has a filter to filter the air allowed into the one or more channels;

wherein the one or more channels are connected so that the same air can flow through all of the one or more channels;

wherein the inner chamber of the housing is separated into a top portion and a bottom portion by a water filter which inhibits a pool of electrolyzed water within the bottom portion of the inner chamber from coming into the top portion of the inner chamber; and and wherein the apparatus further includes a first tube having a first end connected to the top portion of the inner chamber, and an opposing second end, such that the air passes from the top portion of the inner chamber into the first tube through the first end of the first tube, through the first tube, out the opposing second end of the first tube, and out of the inner chamber of the housing.

10. The apparatus of claim 9, further comprising:

an ultraviolet light source within at least one of the one or more channels;

wherein the ultraviolet light source is directed at the air flowing in the one or more channels to cause contaminants in the air to be killed; and wherein the ultraviolet light source is located in a portion of a channel of the one or more channels which is surrounded by the top portion of the inner chamber of the housing.

11. The apparatus of claim 10, further comprising:

a mask configured to attach and detach from the second end of the first tube.

12. The apparatus of claim 9, further comprising:

a mask configured to attach and detach from the second end of the first tube.

13. A method comprising:

filtering a first set of one or more contaminants out of air flowing into an inner chamber of a housing; and causing the first set of one or more contaminants to fall into a pool of electrolyzed water in the inner chamber of the housing by at least in part directing the first set of one or more contaminants by one or more channels in the inner chamber;

wherein the first set of one or more contaminants are filtered by a first filter located at a first end of a first channel of the one or more channels;

wherein the first channel has a second end which opposes the first end;

wherein the first channel and a second channel meet at a junction within the inner chamber of the housing;

wherein the junction is located nearer the second end of the first channel than the first end of the first channel;

wherein a first end of the second channel is within the pool of electrolyzed water located in the bottom portion of the inner chamber; and wherein the inner chamber is separated into a top portion and a bottom portion by a water filter, which inhibits the pool of electrolyzed water, from coming into the top portion of the inner chamber; and and wherein the junction is within the top portion of the inner chamber.

14. The method of claim 13, further comprising:

causing the first set of one or more contaminants in the inner chamber of the housing to be killed by an ultraviolet light source and the pool of electrolyzed water.

15. The method of claim 13, wherein the junction is between an ultraviolet light source and the first end of the second channel.

16. The method of claim 13, wherein the water filter is configured to cover an entire surface area of the pool of electrolyzed water, from one end of the housing to an opposite end of the housing, except for an area where the first end of the second channel is inserted into the pool of electrolyzed water.

17. The method of claim 16, wherein the area where the first end of the second channel is inserted into the pool of electrolyzed water is central in the inner chamber.

18. The method of claim 13, further comprising receiving the air through a first end of the first channel, through the first channel, through the junction into the second channel, and modifying the air in the second channel to form a first modified air;

receiving the first modified air into the pool of electrolyzed water, after the first modified air has passed through and out of the second channel;

modifying the first modified air in the pool of electrolyzed water to form a second modified air;

receiving the second modified air into a tube, after the second modified air has passed out of the pool of electrolyzed water, and through the water filter; and allowing the second modified air to pass out of the tube and out of the inner chamber of the housing.

19. The method of claim 13, wherein there is a gap lying outside of the second channel, between the second channel and the housing, within the inner chamber of the housing; and wherein the air is configured to flow from the pool of electrolyzed water through the gap, into a tube, and out of the housing; and wherein the tube is outside of the first channel, outside of the second channel, and the tube is not directly connected to the first channel or the second channel, such that the air leaving the second channel through the first end of the second channel passes through the pool of electrolyzed water, outside of the second channel, and through the gap, outside of the second channel, to go into the tube, and exit the housing through the tube.

20. A method comprising:

filtering a first set of one or more contaminants out of air flowing into an inner chamber of a housing; and causing the first set of one or more contaminants in the inner chamber of the housing to be killed by an ultraviolet light source and a pool of electrolyzed water;

wherein the first set of one or more contaminants are filtered by a first filter located at a first end of a first channel;

wherein the first channel has a second end which opposes the first end;

wherein the first channel and a second channel meet at a junction within the inner chamber of the housing;

wherein the junction is located nearer the second end of the first channel than the first end of the first channel;

wherein a first end of the second channel is within the pool of electrolyzed water; and wherein the inner chamber is separated into a top portion and a bottom portion by a water filter, which inhibits the pool of electrolyzed water, which is located in the bottom portion of the inner chamber, from coming into the top portion of the inner chamber; and wherein the junction is within the top portion of the inner chamber; and wherein the junction is between the ultraviolet source and the first end of the second channel.

\* \* \* \* \*